US012766088B2

(12) United States Patent
McConaughy et al.

(10) Patent No.: US 12,766,088 B2
(45) **Date of Patent: *Oct. 20, 2026**

(54) SKIN CARE EMULSION COMPOSITION WITH CLEAN POLYMERS AND EMULSIFIERS

(71) Applicant: The Procter & Gamble Company, Cincinnati, OH (US)

(72) Inventors: Shawn David McConaughy, Cincinnati, OH (US); Andrew Michael Hodowanec, Cincinnati, OH (US); Tricia Jean Rist, Mason, OH (US); Thomas Arthur Sturgis, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 435 days.

This patent is subject to a terminal disclaimer.

(21) Appl. No.: 18/335,261

(22) Filed: Jun. 15, 2023

(65) Prior Publication Data

US 2023/0404897 A1 Dec. 21, 2023

Related U.S. Application Data

(60) Provisional application No. 63/352,265, filed on Jun. 15, 2022.

(51) Int. Cl.

*A61K 8/39* (2006.01)
*A61K 8/81* (2006.01)
*A61K 8/92* (2006.01)
*A61Q 19/00* (2006.01)

(52) U.S. Cl.

CPC .............. *A61K 8/8188* (2013.01); *A61K 8/39* (2013.01); *A61K 8/92* (2013.01); *A61Q 19/00* (2013.01); *A61K 2800/10* (2013.01); *A61K 2800/30* (2013.01)

(58) Field of Classification Search

CPC .......... A61K 8/8188; A61K 8/39; A61K 8/92; A61K 2800/10; A61K 2800/30; A61Q 19/00

See application file for complete search history.

(56) References Cited

U.S. PATENT DOCUMENTS

| | | | |
|---|---|---|---|
| 9,956,148 B2 | 5/2018 | Ibe et al. | |
| 10,292,929 B2 | 5/2019 | Burgo et al. | |
| 10,638,755 B2 | 5/2020 | Pesaro et al. | |
| 2014/0147525 A1 | 5/2014 | De Paula et al. | |
| 2015/0265504 A1 | 9/2015 | Crane et al. | |
| 2017/0087074 A1 | 3/2017 | Perusse et al. | |
| 2020/0093712 A1 | 3/2020 | Uchiyama et al. | |
| 2021/0363086 A1* | 11/2021 | Burgo .................... | A61K 8/062 |
| 2022/0009863 A1 | 1/2022 | Nahrwold | |

FOREIGN PATENT DOCUMENTS

| | | | |
|---|---|---|---|
| CN | 107308018 | A | 11/2017 |
| CN | 107375023 | A | 11/2017 |
| CN | 110755352 | A | 2/2020 |
| CN | 112315845 | A | 2/2021 |
| CN | 112704647 | A | 4/2021 |
| JP | 2014156431 | A | 8/2014 |
| JP | 2017155034 | A | 9/2017 |
| JP | 2019094312 | A | 6/2019 |
| JP | 2022021790 | A | 2/2022 |
| KR | 20170033483 | A | 3/2017 |
| KR | 101877211 | B1 | 7/2018 |
| WO | 2016145561 | A1 | 9/2016 |
| WO | 2019082796 | A1 | 5/2019 |
| WO | 2020159121 | A1 | 8/2020 |
| WO | 2021237207 | A2 | 11/2021 |
| WO | 2022112476 | A1 | 6/2022 |

OTHER PUBLICATIONS

KR101877211b1, STIC Translation (Year: 2018).*
KR20170033483A, Machine Translation (Year: 2017).*
CN112704647A, Machine Translation (Year: 2017).*
Mo (KR101877211B1, STIC Translation) (Year: 2018).*
JP2017155034A, J-PlatPat Trarnslation (Year: 2017).*
Duprat-de-Paule et al., Augmented bio-based lipids for cosmetics, OCL Journal vol. 25 No. 5, Jun. 15, 2018, 12 Pages.
Anti-Aging Daily Serum 2.0', Database accession No. 8717269 (XP093093512), May 18, 2021, 3 Pages.
"Glycolic Peel Mask", Database accession No. 8585855 (XP093093519), Mar. 26, 2021, 2 Pages.
"Hand Cream", Database accession No. 3981509 (XP93092670), May 10, 2016, 3 Pages.
"Sustainable anti-oxidant skin care", Retrieved From: https://www.seppic.com/sites/seppic/files/2018/04/02/form-eu07411-sustainable-anti-oxidant-skin-care-powdery-and-dry-finish.pdf, Apr. 2, 2018, 1 Page.
Tightening Daily Super-Mask, Database accession No. 4874621 (XP093093522), Jun. 8, 2017, 5 Pages.
PCT Search Report and Written Opinion for PCT/US2023/068482 dated Nov. 6, 2023, 18 pages.
"Ecostore AU 2021", Retrieved from Internet: https://web.archive.org/web/20210413033254/https://ecostore.com/au/ingredients/approved/cetearyl-alcohol, Apr. 13, 2021, pp. 1-5.

(Continued)

*Primary Examiner* — Jeffrey S Lundgren
*Assistant Examiner* — Ibrahim D Bori
(74) *Attorney, Agent, or Firm* — Alexandra S. Anoff

(57) ABSTRACT

A skin care composition in the form of an emulsion with a continuous phase that includes a polymer and water and a dispersed phase that includes two or more emollients and an emulsifier. The polymer is an acrylate/taurate copolymer that can be compatible with polyglyceryl-3 cetearyl ether olivate, so the composition is a stable emulsion with a viscosity of greater than or equal to 550 Pa*s at a shear rate of 0.10 $s^{-1}$ according to the Rheology Test Method.

18 Claims, 2 Drawing Sheets

(56) References Cited

OTHER PUBLICATIONS

"Phenylpropanol EHG Specification Sheet", Making Cosmetics, Retrieved from Internet: makingcosmetics.com, Nov. 2, 2018, 1 page.
"Safety Assessment of Acryloyldimethyltaurate Polymers as Used in Cosmetics", Cosmetic Ingredient Review, Clariant International LTD, May 24, 2017, pp. 1-21.
"Technical Data Sheet Plantasens® Emulsifier CP5", Clariant, Feb. 2020, pp. 1-2.
Ecostore AU 2020, Retrieved from Internet: https://web.archive.org/web/20200813115244/https://ecostore.com/au/ingredients/approved/cetyl-ethylhexanoate, Aug. 13, 2020, pp. 1-5.
Reply to 'Silicone Alternatives/Soaping', EVchem, Chemists Corner, Element 44 Inc., May 4, 2021, pp. 1-5.
Tafuro el al. "Rheological and Textural Characterization of Acrylic Polymer Water Dispersions for Cosmetic Use", American Chemical Society Ind., Eng. Chem. Res., vol. 28, Dec. 2, 2019, pp. 23549-23558.
All Office Actions; U.S. Appl. No. 18/335,263, filed Jun. 15, 2023.
All Office Actions; U.S. Appl. No. 18/335,268, filed Jun. 15, 2023.
John Woodruff, "Cosmetic preservation", online retrieved from"http://creative-developments.co.uk/wp-content/uploads/2013/10/Cosmetic-Preservation-2014.pdf", XP055432553, Jan. 1, 2014, 06 pages.
U.S. Appl. No. 18/335,263, filed Jun. 15, 2023, to Shawn David McConaughy et al.
U.S. Appl. No. 18/335,268, filed Jun. 15, 2023, to Shawn David McConaughy et al.
Coker et al. "Ludwig's Applied Process Design for Chemical and Petrochemical Plants", Physical Properties of Liquids and Gases, Elsevier Inc. 2007, pp. 103-132.
"Ingredients to Die For", Retrieved from Internet: https://www.ingredientstodiefor.com/item/Caprylic_Capric_Triglycerides/464, Jan. 13, 2014, 03 pages.
Bektas et al., "Sensory Mapping for Common Special Esters in Cream Products", The Online Journal of Science and Technology, vol. 10, Retrieved from Internet: www.tojsat.net, Oct. 2020, pp. 152-157.
SNF, Personal Care Brochure, 2021, pp. 1-28.

* cited by examiner

SKIN CARE EMULSION COMPOSITION WITH CLEAN POLYMERS AND EMULSIFIERS

FIELD OF THE INVENTION

The present disclosure is generally directed towards skin care emulsion compositions that contain clean polymers, in particular the skin care emulsions are stable, viscous compositions that contain clean polymers, such as an acrylate, taurate copolymer and a clean and natural or naturally derived emulsifier, such as polyglyceryl-3 cetearyl ether olivate.

BACKGROUND OF THE INVENTION

Some consumers want skin care products that are efficacious, absorb quickly into the skin, and are formulated without petroleum derived ingredients, ethoxylated ingredients, sulfates, parabens, formaldehydes, phthalates, and mineral oil.

Polymers are frequently used in skin care products to enhance the product's viscosity and can also act as a moisturizer. Many skin care products contain multiple polymers that can include polyacrylamides, petroleum derived ingredients (e.g., isoparaffin, petrolatum), and/or ethoxylated ingredients. However, some consumers prefer products that are formulated without these ingredients and may also want products that meet the requirements to be marketed as "Clean at Sephora" (see *Best Clean Beauty Products* 2022. Sephora. Retrieved Jun. 13, 2022, from www.sephora.com/beauty/clean-beauty-products, "Clean at Sephora" is an initiative in which the beauty retailer badged over 2,000 products as "clean," in this case meaning free of ingredients like sulfates, parabens, formaldehyde, phthalates, and mineral oil).

One polymer that can be used in these clean products is a copolymer of acrylates and taurate (e.g., Sodium Acrylate/Sodium Acryloyldimethyl Taurate Copolymer & C15-19 Alkane & Polyglyceryl-6 Laurate & Polyglycerin-6 available as SEPILIFE™ NUDE from Seppic). This class of polymers may deliver an excellent texture, usage experience and performance, while also meeting the definition of "clean" under the Clean at Sephora standards.

The polymer is generally supplied as a dispersed phase in an oil and is part of the continuous phase of an oil-in-water emulsion. An emulsifier can promote the formation of the emulsion and can also help maintain product stability. However, many traditional emulsifiers do not satisfy the "Clean at Sephora" guidelines and therefore may not be preferred by some consumers. Other emulsifiers are not compatible with the copolymer of acrylates and taurate thickening agent, for instance, the product is not a stable emulsion that has a silky texture that is quickly absorbed into the user's skin.

Therefore, there is a need for one or more emulsifiers that are compatible with a copolymer of acrylates and taurate to form a stable emulsion, are non-ethoxylated, and clean. In some examples, there is also a need for the emulsifier to be natural, naturally derived and/or biodegradable.

SUMMARY OF THE INVENTION

A skin care composition comprising: (a) a continuous phase comprising: (i) a polymer comprising an acrylate/taurate copolymer; (ii) water; (b) a dispersed phase comprising: (i) two or more emollients comprising: (1) a liquid emollient; wherein the liquid emollient comprises alkanes, esters, triglycerides, or combinations thereof; (2) a fatty alcohol having an average carbon chain length ranging from about 12 to about 22; (c) an emulsifier comprising polyglyceryl-3 cetearyl ether olivate.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
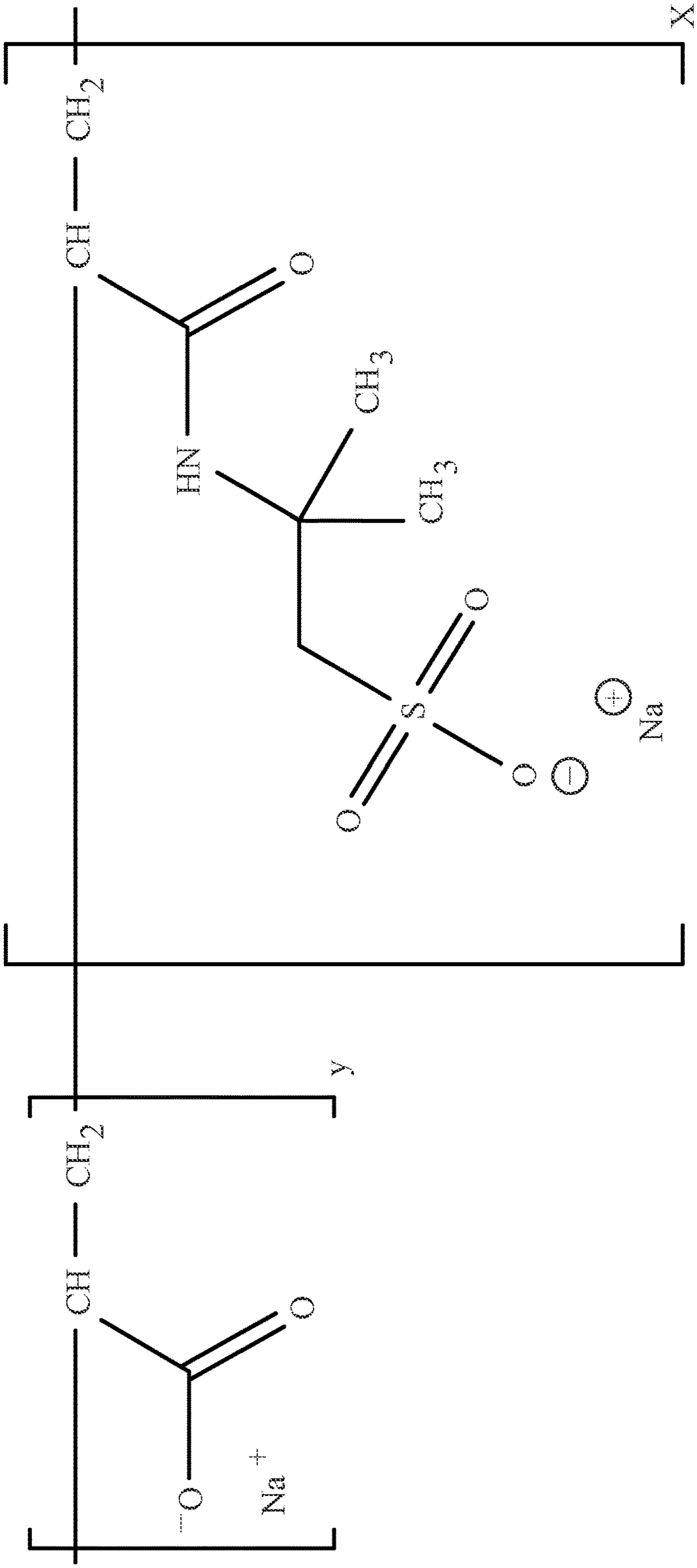
FIG. 1 shows the chemical structure for sodium acrylate/sodium acryloyldimethyl taurate copolymer (and) C15-19 alkane (and) polyglyceryl-6 laurate (and) polyglycerin-6.

Skin care compositions can contain synthetic polymers. The polymers can enhance the composition's texture and viscosity. However, these polymers can contain polyacrylamides, petroleum derived ingredients, and/or ethoxylated ingredients. Some consumers would prefer products that are formulated without these ingredients, while also being clean. It was found that one polymer that can be used in these clean products is a copolymer of acrylates and taurate, for example a sodium acrylate/sodium acryloyldimethyl taurate copolymer like sodium acrylate/sodium acryloyldimethyl taurate copolymer & C15-19 alkane & polyglyceryl-6 laurate & polyglycerin-6 (commercially available as SEPILIFE™ NUDE from Seppic), as shown in FIG. 1. Another polymer that can be used is sodium acrylate/sodium acryloyldimethyl taurate copolymer & C15-19 alkane & Lauryl Glucoside (commercially available as Natursol™ EMI132 from SNF™).

In skin care compositions the polymer is generally supplied within an oil and then inverts to become part of the continuous phase in an oil-in-water emulsion. It can be difficult to form a stable emulsion, particularly if the skin care product is a moisturizer that has a relatively high level of oil. An emulsifier can promote the formation of the emulsion and can also help maintain product stability.

However, it can be difficult to select one or more emulsifiers that efficiently build the composition's viscosity and form stable emulsions in products that contain a copolymer of acrylates and taurate. Furthermore, many consumers want a clean product that can include one or more emulsifiers that are natural, naturally derived, and/or biodegradable.

Also, it can be advantageous for the one or more emulsifiers to be efficient because emulsifiers are generally used at the lowest level that gives the desired product viscosity and stability to give the best product performance. If an emulsifier is only effective when used at a relatively high level, the product may be difficult to spread and can remain as a white layer on top of the skin, instead of absorbing into skin. In these cases, the product can also feel heavy and/or tacky. Furthermore, it can be advantageous if there is synergy between the polymer and the emulsifier, which can allow the emulsifier to be incorporated at an even lower level leading to a smooth lightweight moisturizer with sufficient viscosity.

Skin care compositions can include a range of emollients that can soften, moisturize, and/or protect the skin against irritation as well as aid in solubility of various skin care benefit ingredients. These emollients can have a range of polarity and it can be advantageous to select an emulsifier that is effective in the skin composition system regardless of the polarity of the emollient.

Examples B-J (see Table 1 to Table 3, hereafter) were made with emulsifiers that are clean and natural or naturally derived. These examples are compared to Example A-1 and 2 (see Table 1, hereafter) that include PEG-100 Stearate as the emulsifier, which is currently used in some in-market products. Examples A-1 and 2 have a sufficient viscosity (1082 Pa*s and 842 Pa*s, respectively), which indicates that the emulsifier is compatible with the sodium acrylate/sodium acryloyldimethyl taurate copolymer. However, some consumers prefer skin care products that are formulated without PEG. With respect to Examples B-J, three emulsifiers (see Examples E, G, and H) had sufficient viscosity (e.g., ≥550 Pa*s) with compositions that included a non-polar emollient (isohexadecene) and a more polar emollient (triheptanoin). However, it was found that Examples G and H could be consumer acceptable because not only did the compositions have sufficient viscosity, but did not have a noticeable off-putting smell. Some consumers may prefer products made with Example G, as compared to Example H because Example G has a higher viscosity with both emollients. The emulsifiers in Examples H-1 and 2 were cetearyl olivate and sorbitan olivate (commercially available as Olivem® 1000 from HallStar®). The emulsifier in Examples G-1 and 2 were polyglyceryl-3 cetearyl ether olivate (commercially available as Galolive® Bioten from Acme-Hardesty®). It is believed that similar emulsifiers that include waxy esters made from fatty alcohols and fatty acids derived from natural sources with a carbon chain length ranging from C12-C22 could be compatible with sodium acrylate/sodium acryloyldimethyl taurate copolymer. The composition can include at least 50% natural or naturally derived ingredients, alternatively at least 60%, alternatively at least 70%, alternatively at least 75%, alternatively at least 80%, alternatively at least 85%, and alternatively at least 90%. In some examples, one or more ingredients, in addition to being naturally derived, has greater than 60% natural origin by molecular weight, alternatively greater than 70%, alternatively greater than 80%.

In some examples, the composition can be formulated without, substantially free of, or free of the following ingredients: triethanolamine, ethanol, glycerine monostearate, sodium hydroxide, sodium chloride, tocopherols, and combinations thereof. Some consumers believe these ingredients are irritating and/or can cause acne. In some examples, the composition can be formulated without, substantially free of, or free of silicones.

Furthermore, the composition can be a physically stable emulsion. A composition is physically stable if by visual detection there is no phase separation or the viscosity varies by less than 40% when stored in a glass jar closed finger tight between t=0 (i.e., immediately after the composition is made) and a freeze thaw cycle where the sample is held at −18° C. for 24 hours then returned to room temperature or one month storage at 40° C. followed by return to room temperature. As used herein, "visual detection" means that a human viewer can visually discern if the product had separated into 2 distinct layers in a 2 oz clear glass jar with the unaided eye (excepting standard corrective lenses adapted to compensate for near-sightedness, farsightedness, or stigmatism, or other corrected vision) in lighting at least equal to the illumination of a standard 100-watt incandescent white light bulb at 30 cm.

All percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

Definitions

As used herein, "biodegradable" refers to materials that meet the pass levels for readily and ultimate biodegradability according to the OECD Guideline for Testing of Chemicals, Method 301 B: CO2 Evolution (Modified Sturm Test) (adopted Jul. 17, 1992).

As used herein, "clean" refers to cosmetic compositions that are formulated without the following ingredients: Acrylate Monomers, Aluminum Salts, Animal Musk's/Fats/Oils, Benzophenones and related compounds, Butoxyethanol, Butylated hydroxyanisole (BHA), Butylated hydroxytoluene (BHT), Carbon Black or Black 2, Coal Tar, Ethanolamines, Formaldehyde and Formaldehyde-releasing agents, Hydroquinone, Lead and Lead Acetate, Mercury and Mercury Compounds (Thimerisol), Methoxyethanol, Methyl Cellosolve, Methylchloroisothiazolinone and Methylisothiazolinone, Mineral Oil, Nanomaterials, Chemical sunscreens (including oxybenzone, avobenzone, and octinoxate), Parabens (including butyl-, methyl-, and propylparaben), Petrolatum and Paraffin, Phenoxyethanol, Phthalates, Plastic Microbeads, Polyacrylamide and Acrylamide, Resorcinol, Retinyl Palmitate, Styrene, Sulfates (including sodium lauryl sulfate and sodium laureth sulfate), Talc, Toluene, Triclosan and Triclocarban, Acetaldehyde, Acetone, Acetonitrile, Benzalkonium chloride, Bisphenol A (BPA), Ethylenediaminetetraacetic acid (EDTA), Methylene chloride, Polytetrafluoroethylene (PTFE), Perfluorooctanoic acid (PFOA), 1,4 Dioxane, Octinoxate, Nitromusks and Polycyclic Musks, PFAS compounds, Ethoxylated Ingredients, Polyethylene glycol (PEG), Cyclic Silicones, volatile linear silicones including silicone elastomers which contain volatile linear silicones, and derivatives and combinations thereof.

As used herein, "formulated without" means that the ingredient is not intentionally added. However, "formulated without" does not guarantee "100% free from" since trace contaminants are possible.

As used herein, "natural" refers to cosmetic ingredients obtained only from plants, animals, micro-organisms, or minerals according to International Organization for Standardization 16128-1, Part 1, ¶2.1 (Feb. 15, 2016). Ingredients obtained from fossil fuels are excluded from the definition. A non-limiting list of "natural" ingredient sources can include olive, palm, corn, palm, rapeseed, soybean, sunflower, coconut, tallow, canola, castor, and combinations hereof.

As used herein, "naturally derived" refers to cosmetic ingredients of greater than 50% natural origin by molecular weight, by renewable carbon content or by any other relevant methods, obtained through defined chemical and/or biological processes with the intention of chemical modification according to ISO 16128-1, Part 1, ¶3.1 (Feb. 15, 2016). ISO 16128-1, Appendix B includes a non-limiting list of chemical and biological processes for derived natural ingredients, which is incorporated by reference.

As used herein, "skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin; preventing damage to skin via anti-oxidant approaches, including UV A and UV B induced damage, preventing formation of comedones, balancing the skin microbiome or preventing acne.

As used herein, "skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

As used herein, "skin care composition" means a composition that includes a skin care active and regulates and/or improves skin condition.

As used herein, "substantially free" means less than 0.5%, less than 0.25%, less than 0.1%, less than 0.05%, and/or less than 0.01%.

Composition

The skin care composition can be a stable emulsion with a continuous aqueous phase (e.g., an oil-in-water or water-in-oil-in-water emulsion) or a continuous oil phase (e.g., water-in-oil or oil-in-water-in-oil emulsion) and a dispersed phase. An emulsifier can promote the formation of the emulsion and can also help maintain product stability.

In some examples, the skin care composition can be a moisturizer with a viscosity that is sufficient for it to be dispensed from a jar without sloshing or easily spilling and is also thin enough so it can be easily spread across a user's face, eye area, and/or neck. The viscosity at about 0.10 $s^{-1}$ can be greater than or equal to 550 Pa*s, alternatively greater than or equal to 600 Pa*s, alternatively greater than or equal to 750 Pa*s, alternatively greater than or equal to 900 Pa*s, alternatively greater than or equal to 1500 Pa*s, alternatively greater than or equal to 2000 Pa*s, alternatively greater than or equal to 2500 Pa*s, alternatively greater than or equal to 3000 Pa*s. The average viscosity can be from about 550 Pa*s to about 6000 Pa*s, alternatively from about 600 Pa*s to about 5500 Pa*s, alternatively from about 800 Pa*s to about 5000 Pa*s, alternatively from about 900 Pa*s to about 4500 Pa*s, and alternatively from about 1000 Pa*s to about 3000 Pa*s. The viscosity at about 0.10 $s^{-1}$ can be determined by the Rheology Test Method, described hereafter.

In some examples, the composition can be a serum with a viscosity at about 0.10 $s^{-1}$ from about 20 to about 500 Pa*s, alternatively from about 30 to about 300 Pa*s, and alternatively from about 50 to about 20 Pa*s. In some examples, the composition can be a serum that is dispensed through a pump dispenser and has a viscosity of less than or equal to 500 Pa*s. In other examples, the composition can be a serum that is dispensed through a dropper with a viscosity of less than or equal to 200 Pa*s.

In some examples, the composition can have a limited number of ingredients, in particular a limited number of ingredients that need to be reported on the INCI (International Nomenclature Cosmetic Ingredient) statement on the package. The composition can ≤25 ingredients, alternatively ≤20 ingredients, alternatively ≤15 ingredients, and alternatively ≤12 ingredients.

Emulsifier

The skin care composition can contain an emulsifier. The preferred emulsifier can promote the formation of the emulsion, stabilize the composition, and can work with the polymer to thicken the skin care composition.

The skin care composition can contain from about 0.10% to about 2%, alternatively from about 0.2% to about 1.5%, alternatively from about 0.4% to about 1.2%, and alternatively from about 0.6% to about 0.8% of an emulsifier. The skin care composition can contain less than 2%, alternatively less than 1.75%, alternatively less than 1.5%, alternatively less than 1.25%, alternatively less than 1%, and alternatively less than 0.8% of an emulsifier.

The emulsifier can be polyglyceryl-3 cetearyl ether olivate (commercially available as Galolive® Bioten from Acme-Hardesty®).

In another example, the emulsifier can be cetearyl olivate and sorbitan olivate (commercially available as Olivem® 1000 from HallStar®).

Continuous Phase

The continuous phase can comprise one or more of the following: a dermatologically acceptable carrier, polymer, Vitamin $B_3$ compound, or a combination thereof.

Dermatologically Acceptable Carrier

The continuous phase can include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 95%, about 52% to about 90%, about 55% to about 85%, or, alternatively, from about 60% to about 80%, by weight of the composition.

The carrier can be in a wide variety of forms. In some instances, the solubility or dispersibility of the components (e.g., extracts, sunscreen active, additional components) may dictate the form and character of the carrier. Non-limiting examples of the product form can include dispersions, emulsions, and solid forms (e.g., gels, sticks, flowable solids, or amorphous materials). The skin care composition can be aqueous or anhydrous. The oil phase of the emulsion may include silicone oils, esters, ethers, triglcyerides and mixtures thereof. The aqueous phase may include water and water-soluble ingredients (e.g., water-soluble moisturizing agents, conditioning agents, anti-microbials, humectants and/or other skin care actives). In some instances, the aqueous phase may include components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s). The composition can contain from about 1% to about 20%, alternatively from about 3% to about 18%, alternatively from about 5% to about 17%, and alternatively from about 6% to about 15% humectant.

In some instances, the compositions herein are in the form of an oil-in-water ("0/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more non-volatile oils (e.g., botanical oils and/or silicone oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable diluents. As used herein, "diluent" refers to materials in which the skin care actives herein can be dispersed, dissolved, or otherwise incorporated. Some nonlimiting examples of hydrophilic diluents include water, organic hydrophilic diluents such as lower monovalent alcohols (e.g., $C_1$-$C_4$) and low molecular weight glycols and polyols, glycerol, butylene glycol, 1,2,4-butanetriol, sorbitol esters, 1,2,6-hexanetriol, ethanol, isopropanol, sorbitol esters, butanediol, ether propanol, and combinations thereof.

Polymer

The continuous phase can include one or more polymers in the water phase. The polymer can help thicken the skin care composition, as well as help provide a smooth, silky feeling during and after application to the skin.

The composition may comprise greater than 0.2%, alternatively greater than 0.3%, alternatively greater than 0.4%, alternatively greater than 0.5%, alternatively greater than 0.6%, alternatively greater than 0.7%, or alternatively greater than or equal to 0.8% polymer. The composition may comprise less than or equal to 1.6%, alternatively less than or equal to 1.4%, alternatively less than or equal to 1.3%, alternatively less than or equal to 1.0% polymer. In some examples, the composition is a moisturizer, such as a cream or lotion, and can include from about 0.2% to about 3%, alternatively from about 0.5% to about 2.5%, alternatively from about 0.75% to about 2.2%, alternatively from about 1.2% to about 2%, alternatively from about 1.5% to about 1.9%, or alternatively from about 1.6% to about 1.8% polymer. In other examples, the composition can be a serum and can include from about 0.1% to about 1.5%, alternatively from about 0.2% to about 1.25%, alternatively from about 0.4% to about 1%, or alternatively from about 0.5% to about 0.75% polymer.

The polymer can include an acrylate/taurate copolymer and in some examples the polymer can be a sodium acrylate/sodium acryloyldimethyl taurate copolymer. In some examples, the composition can include Sodium Acrylate/Sodium Acryloyldimethyl Taurate Copolymer & C15-19 Alkane & Polyglyceryl-6 Laurate & Polyglycerin-6 (commercially available as SEPILIFE™ NUDE from Seppic® Corporation). In some cases, the composition can include sodium acrylate/sodium acryloyldimethyl taurate copolymer & C15-19 alkane & Lauryl Glucoside (commercially available as Natursol™ EMI132 from SNF Floerger). In other examples, the composition can include sodium polyacryloyldimethyl taurate, hydroxyethyl acrylate/sodium acrloyldimethyl taurate copolymer, Sodium acrylate/Sodium Acryloyldimethyl Taurate copolymer, Ammonium Polyacryloyldimethyl taurate, Ammonium Acryloyldimethyltaurate/VP Copolymer, sodium acrylates copolymer, Polyacrylate Crosspolymer-11, Polyacrylate Crosspolymer-6, carbomer, Acrylates/C10-30 Alkyl Acrylate Crosspolymer, and combinations thereof.

Vitamin $B_3$ Compound

The compositions herein can include a safe and effective amount of a vitamin $B_3$ compound. The Vitamin $B_3$ compound can be in the continuous phase. In some instances, the present compositions may contain 0.01% to 10%, by weight, of the vitamin $B_3$ compound, based on the weight or volume of the composition (e.g., 0.1% to 10%, 0.5% to 5%, or even 1% to 3%). As used herein, "vitamin $B_3$ compound" means a compound having the formula:

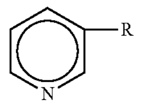

Where: R is $CONH_2$ (i.e., niacinamide), COOH (i.e., nicotinic acid) or CH 2 OH (i.e., nicotinyl alcohol); derivatives thereof; and salts of any of the foregoing.

Exemplary derivatives of vitamin B3 compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide.

Thickening Agents

The continuous phase can include one or more thickening agents. The thickening agent can include natural gums, cellulose thickening agents, natural powders, or a combination thereof.

Natural gums are polysaccharides of natural origin, capable of causing a viscosity increase in solution, even at small concentrations. They can be used as thickening agents, gelling agents, stabilizers, and can help keep the emulsion more stable. Most often these gums are found in the woody elements of plants or in seed coatings. Natural gums can be classified according to their origin. They can also be classified as uncharged or ionic polymers (polyelectrolytes), examples of which include the following: Natural gums obtained from seaweeds, such as: agar; alginic acid; sodium alginate; and carrageenan. Natural gums obtained from non-marine botanical resources can include: gum arabic, from the sap of *Acacia* trees; gum ghatti, from the sap of *Anogeissus* trees; gum tragacanth, from the sap of *Astragalus* shrubs; karaya gum, from the sap of *Sterculia* trees. Examples of uncharged gums include: guar gum, from guar beans, locust bean gum, from the seeds of the carob tree; beta-glucan, from oat or barley bran; chicle gum, an older base for chewing gum obtained from the chicle tree; dammar gum, from the sap of Dipterocarpaceae trees; glucomannan from the konjac plant; mastic gum, a chewing gum from ancient Greece obtained from the mastic tree; psyllium seed husks, from the *Plantago* plant; spruce gum, a chewing gum of American Indians obtained from spruce trees; tara gum, from the seeds of the tara tree. Natural gums produced by bacterial fermentation include gellan gum and xanthan gum.

Examples of cellulose thickening agents which may be used in the skin care compositions can include, but are not limited to, hydroxyethylcellulose, hydroxypropyl cellulose, hydroxypropyl methylcellulose, microcrystalline cellulose, or a combination thereof.

Natural powders can include, for example, clay, diatomaceous earth, fuller's earth, silica, silica shells or spherical silica, fumed silica, spherical silica, hydrated silica, silica silylate, mica, titanated mica, talc, corn starch, rice starch, glyceryl starch, soy flour, walnut shell powder, agar, sericite, dextran, nylon, silk powder, chalk, calcium carbonate, bismuth oxychloride, iron oxide, titanium dioxide, aluminum silicate, magnesium aluminum silicate, calcium silicate, magnesium trisilicate, aluminum starch octenylsuccinate, bentonite, hectorite, kaolin, maltodextrin, montmorillonite, zinc laurate, zinc myristate, zinc rosinate, alumina, attapulgite, tin oxide, titanium hydroxide, trimagnesium phosphate, or a mixture thereof.

Dispersed Phase

The dispersed phase can comprise an emollient.

Emollient

The composition may include one or more emollients that can be natural or naturally derived and/or biodegradable, alternatively all the emollients can be natural or naturally derived and/or biodegradable. The skin care composition can be formulated without, free of, or substantially free of petroleum-based emollients. The emollient can be a liquid emollient having a melting point below 40° C., below 35° C., or below 30° C. The liquid emollient can be an oil, which can include an ester, alkane, triglyceride, non-volatile silicones, and combinations thereof. In another example, the emollient can be a waxy emollient, such as a fatty alcohol, having a melting point above 40° C., alternatively above 50° C. In some examples, the skin care composition can contain one or more liquid emollients and one more waxy emollients.

The skin care composition can include from about 1% to about 30%, alternatively from about 2% to about 20%, alternatively from about 3% to about 15% emollient, alternatively from about 4% to about 10%, and alternatively from about 5% to about 8% of one or more emollients.

Liquid Emollient

The skin care composition may include from about 0.5% to about 10%, alternatively from about 1% to about 9%, alternatively from about 1% to about 8%, alternatively from about 2% to about 7%, alternatively from about 3% to about 6% liquid emollient.

The liquid emollient can be a naturally derived oil that is a plant oil. Examples of the plant oil can include, but are not limited to, palm kernel, coconut, avocado, canola, corn, cottonseed, olive, palm, hi-oleic sunflower, mid-oleic sunflower, sunflower, palm stearin, palm kernel olein, safflower, babassu oils, and combinations thereof. In one embodiment, palm kernel oil may be the selected oil. In another embodiment, coconut oil may be the selected oil. In another embodiment, the plant oil may be a combination of palm kernel oil and coconut oil.

The skin care composition can include one or more of the following liquid emollients:

An alkane or isoalkane, ranging in total carbon from about C8-C60, including but not limited to squalane, squalene, coconut alkanes, coconut/palm kernel alkanes, C9-12 Alkane, C10-13 Alkane, C13-15 Alkane, C15-19 Alkane, C14-22 Alkane, C30-34 Alkane, C9-20 Isoalkane, C10-12 Isoalkane, C12-15 Isoalkane, isohexadecene, C32-54 Isoalkane, or a combination thereof.

An ester formed from an alcohol having from 1-6 carbons and acid having from about 6-22 carbons, including but not limited to isopropyl isostearate, isopropyl palmitate, isoamyl laurate, shea butter ethyl esters, shea butter cetyl esters, shea butter decyl esters, shea butter oleyl esters, jojoba esters, coco-capylate/caprate, ethyl caprate, ethylhexyl caprate, isoamyl caprylate/caprate, argan oil isostearyl esters, babassu seed oil ethyl esters, camelina sative seed oil ethyl esters, castor/olive oil esters, coconut oil decyl esters, coconut oil ethyl esters, linseed oil ethyl esters, olive oil decyl esters, olive oil ethylhexyl esters, palm kernel oil triacetin esters, palmitoyl serine/silk amino acid methyl esters, rapeseed oil decyl esters, safflower seed oil decyl esters, sunflower seed oil cetyl esters, sunflower seed oil ethyl esters, trehalose isostearate esters, or a combination thereof.

A triglyceride having 3 carbon chains where the carbon chain length ranges from about C7-C18, including but not limited to triheptanoin, caprylic/capric triglycride, C10-19 triglycerides, caprylic/capric/lauric triglycerides, hydrogenated C12-C18 triglycerides, triethylhexanoin, or a combination thereof.

A non-volatile silicone fluid including but not limited to dimethicone, amodimethicone, or a combination thereof.

Waxy Emollient

The skin care composition may include from about 0.1% to about 10%, alternatively from about 0.2% to about 8%, alternatively from about 0.5% to about 5%, alternatively from about 1% to about 4%, alternatively from about 1.5% to about 3.5%, and alternatively from about 2% to about 3% waxy emollient.

One or more emollients can be solids at room temperature and have an average carbon chain length ranging from about 12 to about 22, alternatively about 12 to about 18, alternatively from about 16 to about 22, and alternatively 16 to about 18.

The skin care composition can include a waxy emollient, such as a wax, butter, fatty alcohol, or a combination thereof. Waxy emollients can include, but are not limited to, beeswax, jojoba wax, shea butter, palm kernel wax, lanolin wax, shellac wax, rice bran wax, carnauba wax, ozokerite, *Cocos nucifera* (coconut) butter, goat butter, *Acrocomia aculeata* seed butter, chiuri butter, carnauba, candelilla, or a combinations thereof.

Fatty alcohols can include monohydric alcohols having 8-22 carbon atoms, although longer chain alcohols in excess of 30 carbons may be used. The fatty alcohols may be saturated or unsaturated. The fatty alcohols may be straight or branched. In one example, the waxy emollient may comprise straight chain, saturated fatty alcohol with a terminal hydroxyl. The fatty alcohols can include decyl alcohol, lauryl alcohol, myristyl alcohol, cetyl alcohol, stearyl alcohol, isostearyl alcohol, icosyl alcohol, behenyl alcohol, batyl alcohol, arachidyl alcohol, brassica alcohol, coconut alcohol, hydrogenated jojoba alcohol, jojoba alcohol, or a combination thereof. In some examples, the fatty alcohol can have an average carbon chain length from about 12 to about 22, alternatively from about 16 to about 22, alternatively from about 16 to about 18. Alternatively, the fatty alcohol can have an average chain length of from about 12 to about 18. In some examples, the skin care compositions can be formulated without, substantially free of, or free of cetearyl alcohol because they believe that it can have unfavorable comedogenicity. In another example, the skin care compositions can be formulated without, substantially free of, or free of palmitic acid and stearic acid.

Other Optional Ingredients

The present composition may optionally include one or more additional ingredients commonly used in cosmetic compositions (e.g., dyes, pigments, mica, insoluble particles, skin care actives, anti-inflammatory agents, sunscreen agents, emulsifiers, buffers, rheology modifiers, chelants, combinations of these and the like), provided that the additional ingredients do not undesirably alter the skin health or appearance benefits provided by the present compositions. The additional ingredients can be in the continuous phase and/or the dispersed phase. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. In some examples, the composition can include a fragrance, in particular a natural fragrance, or a colorant, in particular a natural colorant. In some examples, the skin care composition can include a silicone elastomer including but not limited to silicone elastomers supplied solvated in non-volatile linear silicone fluids, silicone elastomers supplied solvated in alkanes, esters or triglycerides. The chelant can be selected from ethylenediaminetetraacetic acid (EDTA), trisodium ethylenediamine disuccinate (EDDS), trisodium dicarboxymethyl alaninate, tetrasodium glutamate diacetate, phytic acid, or a combination thereof. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; and 6,174,533.

When including optional ingredients in the compositions herein, it may be desirable to select ingredients that do not form complexes or otherwise undesirably interact with other ingredients in the composition, especially pH sensitive ingredients like niacinamide, salicylates and peptides. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

In some examples, the composition can be formulated without, substantially free of, or free of dyes.

Method of Use

The skin care cream/moisturizer composition may be applied to the face, neck, and/or a portion or combination thereof at least once a day, twice a day, or on a more frequent daily basis, during a treatment period. When applied twice daily, the first and second applications are separated by at least 1 to 12 hours. Typically, the composition is applied in the morning and/or at night before bed. The treatment period herein is ideally of sufficient time for the skin care actives to improve the appearance of the skin. The treatment period may last for at least a week (e.g., about 1 week, about 2 weeks, about 4 weeks, about 8 weeks, or even about 12 weeks). In some instances, the treatment period will extend over multiple months (i.e., about 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The skin care composition can be intended for use before bedtime and/or in the morning. It can be evenly massaged over the entire face (including or excluding the eye area) and/or neck. The product can be the final step in a skin care routine and can be applied after cleansing and optionally after applying serums and/or other skin care products. The skin care composition can hydrate to a visibly firm skin for a lifted look. The skin composition can strengthen skin's moisture barrier for bouncy, firm, and younger-looking skin. The skin care composition can reduce and/or soften wrinkles and fine lines.

Test Methods

Rheology Test Method

This method provides a suitable means of measuring the viscosity of the compositions herein. The instrument used in this method is a TA Instruments brand rheometer, or equivalent. The instrument is set up to conduct a rotational ramp under controlled stress conditions, from 0.01 to 2000 Pa over 240 seconds, using serrated parallel plate for the upper and lower geometry with a 40 mm diameter, and a 1.0 mm gap. The temperature is set to 25° C. The instrument protocol is set up to collect 100 data points per decade in a logarithmic distribution, with a setting to stop the measure when shear rates exceed 110 $s^{-1}$.

After conducting an automated gap calibration, approximately 5 grams of a sample is placed on the center of the plate. The plate is positioned to provide a gap of 1.05 mm, and any excess material squeezed out of the perimeter gap of the parallel plates is carefully trimmed away. The plate is then moved the final 0.05 mm to provide a 1.00 mm gap, and the measurement is initiated. At the end of the run, the data file is saved for subsequent plotting and analysis. The viscosity is reported in units of Pascal-Seconds (PaS) as the value at or near a shear rate of 0.10 $s^{-1}$.

EXAMPLES

The following data and examples are provided to help illustrate the skincare compositions described herein. The exemplified compositions are given solely for the purpose of illustration and are not to be construed as limitations of the present disclosure, as many variations thereof are possible without departing from the spirit and scope of the disclosure. All parts, percentages, and ratios herein are by weight unless otherwise specified.

The Examples in Table 1 to Table 12, below, were prepared by the following method. First, a water phase was made by combining water and water soluble ingredients including, but not limited to, glycerin, chelant (e.g., disodium EDTA, EDDS), water soluble skin care actives (e.g., panthenol), and antioxidants (e.g., hydroxyacetophenone). The water phase was mixed and heated to about 50° C. until the ingredients were in solution and/or dispersed. The water phase can contain about 70% to about 98%, alternatively from about 75% to about 95%, alternatively from about 80% to about 94%, alternatively from about 85% to about 93%, or alternatively from about 88% to about 92% water, by weight of the water phase.

In a second container, an oil phase premix was made. The premix included the liquid and waxy emollients and one or more emulsifiers. The premix was mixed and heated to about 50° C. until the ingredients are fully dispersed in the premix.

The premix was added to the water phase. Then, the mixture was milled to emulsify the oil phase premix into the water phase, forming an emulsion where the water phase is the continuous phase, and the oil phase is dispersed phase. One or more additional ingredients were added after emulsification while continuously mixing with an overhead mixer. Additional ingredients may be added either before, after or during cooling of the product to room temperature and included but were not limited to polymeric thickeners (e.g., SEPILIFE™ NUDE, NATURSOL™ EMI 132), silicones, colorants, pigments, powders, micas, preservatives, fragrances, and additional skin actives.

The viscosity of the Examples in the following Tables was determined using the Rheology Test Method, as disclosed herein.

Figure 2:
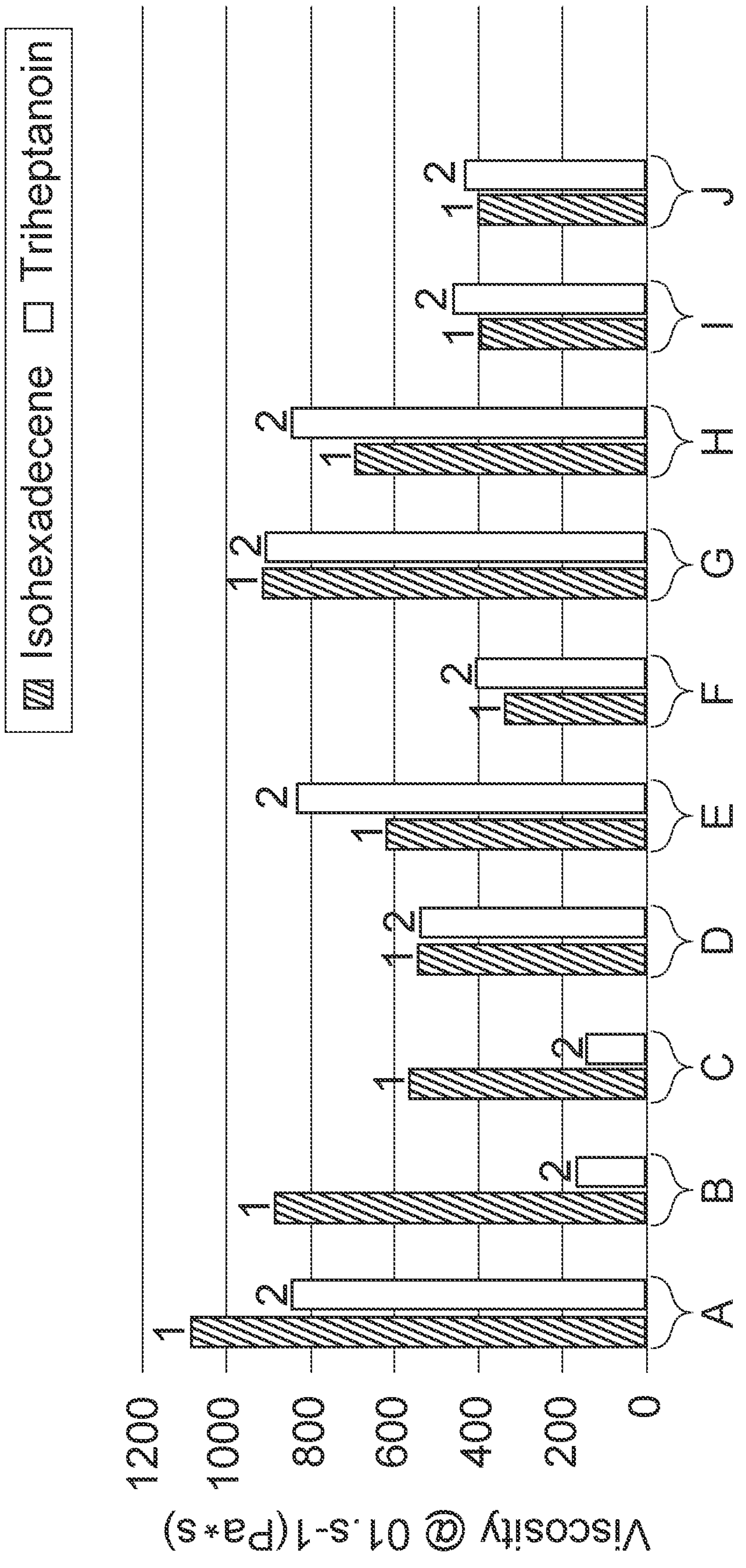
FIG. 2 is a graph showing the viscosity of skin care compositions with an emollient containing either isohexadecene or triheptanoin and differing emulsifiers.

For the Examples detailed in Table 1 to Table 3, below, and FIG. 2, various clean, natural and/or naturally derived emulsifiers that were free of cetearyl alcohol were tested in skin care compositions that included, among other ingredients, a sodium acrylate/sodium acryloyldimethyl taurate copolymer. Each emulsifier was tested in a composition with an emollient that included either isohexadecene, a non-polar hydrocarbon oil, or triheptanoin, a triglyceride that is a more polar, as compared to isohexadecene. The emulsifier may be consumer acceptable if it helped build sufficient viscosity, as indicated when the composition had a viscosity greater than or equal to 550 Pa*s, according to the Rheology Test Method, described herein. This viscosity is considered the minimum necessary to create an acceptable composition that can be packaged in a jar that is open during consumer use, compositions with higher viscosities may be more consumer preferred and in some examples the viscosity can be increased by adding more emulsifier and/or polymer. It can be preferred to select an emulsifier that yields a composition with sufficient viscosity with both isohexadecene and triheptanoin emollients because this shows that the emulsifier builds viscosity across a range of products with different emollient polarities. Also, many skin care products use more than one emollient with different polarities to aid in solubility of various skin care benefit ingredients including ingredients that improve skin texture, tone, or protect against UV damage.

Some examples were made with modified corn starch and others were made with *Zea mays* corn starch (commercially available as AMAZE® HTP Pure from Nouryon®). It was found that there was no appreciable difference in viscosity and stability when formulating with either starch. It was found that *Zea mays* corn starch may be preferred in some large-scale productions.

TABLE 1

| | Ex. A-1 (wt. %) | Ex. A-2 (wt. %) | Ex. B-1 (wt. %) | Ex. B-2 (wt. %) | Ex. C-1 (wt. %) | Ex. C-2 (wt. %) | Ex. D-1 (wt. %) | Ex. D-2 (wt. %) |
|---|---|---|---|---|---|---|---|---|
| Sodium Acrylate/Sodium Acryloyldimethyl Taurate Copolymer & C15-19 Alkane & Polyglyceryl-6 Laurate & Polyglycerin-6[1] | 1.6 | 1.6 | 1.6 | 1.6 | 1.6 | 1.6 | 1.6 | 1.6 |
| Panthenol | 1 | 1 | 1 | 1 | 1 | 1 | 1 | 1 |
| Glycerin | 15 | 15 | 15 | 15 | 15 | 15 | 15 | 15 |
| Niacinamide | 5 | 5 | 5 | 5 | 5 | 5 | 5 | 5 |
| Ethylenediaminetetraacetic acid (EDTA) | 0.05 | 0.05 | 0.05 | 0.05 | 0.05 | 0.05 | 0.05 | 0.05 |
| Hydroxyacetophenone | 0.15 | 0.15 | 0.15 | 0.15 | 0.15 | 0.15 | 0.15 | 0.15 |
| Modified Corn Starch | | | 5 | 5 | 5 | 5 | 5 | 5 |
| *Zea Mays* Corn Starch[2] | 5 | 5 | | | | | | |
| Phenoxyethanol | 0.375 | 0.375 | 0.375 | 0.375 | 0.375 | 0.375 | 0.375 | 0.375 |
| Ethylhexylglycerin | 0.2 | 0.2 | 0.2 | 0.2 | 0.2 | 0.2 | 0.2 | 0.2 |
| Isohexadecene | 6 | | 6 | | 6 | | 6 | |
| Triheptanoin | | 6 | | 6 | | 6 | | 6 |
| Isoamyl Laurate[3] | 3 | 3 | 3 | 3 | 3 | 3 | 3 | 3 |
| Stearyl Alcohol | 1 | 1 | 1 | 1 | 1 | 1 | 1 | 1 |
| Cetyl Alcohol | 0.8 | 0.8 | 0.8 | 0.8 | 0.8 | 0.8 | 0.8 | 0.8 |
| Behenyl Alcohol | 0.6 | 0.6 | 0.6 | 0.6 | 0.6 | 0.6 | 0.6 | 0.6 |
| PEG-100 Stearate | 0.2 | 0.2 | | | | | | |
| Polyglyceryl-3 Methylglucose Distearate[4] | | | 0.2 | 0.2 | | | | |
| Polyglyceryl-10 Diisostearate[5] | | | | | 0.2 | 0.2 | | |
| Polyglyceryl-6 Distearate[6] | | | | | | | 0.2 | 0.2 |
| Water | Q.S. to Volume | | | | | | | |
| Viscosity (Pa*s) | 1082 | 877 | 167 | 480 | 560 | 141 | 542 | 534 |

TABLE 2

| | Ex. E-1 (wt. %) | Ex. E-2 (wt. %) | Ex. F-1 (wt. %) | Ex. F-2 (wt. %) | Ex. G-1 (wt. %) | Ex. G-2 (wt. %) |
|---|---|---|---|---|---|---|
| Sodium Acrylate/Sodium Acryloyldimethyl Taurate Copolymer & C15-19 Alkane & Polyglyceryl-6 Laurate & Polyglycerin-6[1] | 1.6 | 1.6 | 1.6 | 1.6 | 1.6 | 1.6 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Ethylenediaminetetraacetic acid (EDTA) | 0.05 | 0.05 | 0.05 | 0.05 | 0.05 | 0.05 |
| Hydroxyacetophenone | 0.15 | 0.15 | 0.15 | 0.15 | 0.15 | 0.15 |
| Modified Corn Starch | 5 | 5 | 5 | | | |
| *Zea Mays* Corn Starch[2] | | | | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Isohexadecene | 6 | | 6 | | 6 | |
| Triheptanoin | | 6 | | 6 | | 6 |
| Shea Butter Ethyl Esters | | | 3 | 3 | | |
| Isoamyl Laurate[3] | 3 | 3 | | | 3 | 3 |
| Stearyl Alcohol | 1 | 1 | 1 | 1 | 1 | 1 |
| Cetyl Alcohol | 0.8 | 0.8 | 0.8 | 0.8 | 0.8 | 0.8 |
| Behenyl Alcohol | 0.6 | 0.6 | 0.6 | 0.6 | 0.6 | 0.6 |
| Polyglyceryl-3 Distearate (and) Glyceryl Stearate Citrate[7] | 0.2 | 0.2 | | | | |
| Glyceryl Stearate[8] | | | 0.2 | 0.2 | | |
| Polyglyceryl-3 Cetearyl Ether Olivate[9] | | | | | 0.2 | 0.2 |
| Water | Q.S. to Volume | | | | | |
| Viscosity (Pa*s) | 615 | 827 | 335 | 402 | 911 | 906 |

TABLE 3

| | Ex. H-1 (wt. %) | Ex. H-2 (wt. %) | Ex. I-1 (wt. %) | Ex. I-2 (wt. %) | Ex. J-1 (wt. %) | Ex. J-2 (wt. %) |
|---|---|---|---|---|---|---|
| Sodium Acrylate/Sodium Acryloyldimethyl Taurate Copolymer & C15-19 Alkane & Polyglyceryl-6 Laurate & Polyglycerin-6[1] | 1.6 | 1.6 | 1.6 | 1.6 | 1.6 | 1.6 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Ethylenediaminetetraacetic acid (EDTA) | 0.05 | 0.05 | 0.05 | 0.05 | 0.05 | 0.05 |
| Hydroxyacetophenone | 0.15 | 0.15 | 0.15 | 0.15 | 0.15 | 0.15 |
| 43w*Zea Mays* Corn Starch[2] | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Isohexadecene | 6 | | 6 | | 6 | |
| Triheptanoin | | 6 | | 6 | | 6 |
| Shea Butter Ethyl Esters | | | 3 | 3 | | |
| Isoamyl Laurate[3] | 3 | 3 | | | 3 | 3 |
| Stearyl Alcohol | 1 | 1 | 1 | 1 | 1 | 1 |
| Cetyl Alcohol | 0.8 | 0.8 | 0.8 | 0.8 | 0.8 | 0.8 |
| Behenyl Alcohol | 0.6 | 0.6 | 0.6 | 0.6 | 0.6 | 0.6 |
| Cetearyl Olivate, Sorbitan Olivate[10] | 0.2 | 0.2 | | | | |
| Sucrose Polystearate (and) Cetearyl Alcohol (and) *Olea Europaea* (Olive) Oil Unsaponifiables[11] | | | 0.2 | 0.2 | | |
| Glyceryl Oleate (and) Polyglyceryl-3-polyricinoleate (and) *Olea Europaea* (Olive) Oil Unsaponifiables[12] | | | | | 0.2 | 0.2 |
| Water | Q.S. to Volume | | | | | |
| Viscosity (Pa*s) | 692 | 839 | 393 | 454 | 398 | 431 |

Tradenames and Suppliers for Table 1 to Table 3:

1. SEPILIFE™ NUDE from Seppic® Corporation plant-based & renewable
2. AMAZE® HTP Pure from Nouryon®
3. Mackaderm® LIA MB from Solvay
4. TEGO® Care 450 MB from Evonik
5. Barfix H from Barnet® Products
6. Plurol® Stearique MB from Gattefossé®
7. Dermofeel® NC MB from Evonik®
8. HallStar® GMS Pure from Hallstar®
9. Galolive® Bioten from Acme-Hardesty®
10. Olivem® 1000 from HallStar®
11. Plantasens® Natural Emulsifier HP10 from Clariant®
12. Plantasens® Emulsifier CP5 from Clariant®

The emulsifier used in Examples A-1 and 2 is an emulsifier that is used in some in-market products. This emulsifier includes PEG-100 stearate, a polyethylene glycol ester of stearic acid. Skin care compositions with this emulsifier are known to have acceptable viscosity, stability, and product performance. However, some consumers prefer compositions that are free from PEG, natural or naturally derived, and/or biodegradable.

Examples B-J include emulsifiers that are free of PEG and are also clean. In addition, the emulsifiers in Examples B-J are natural or naturally derived, and biodegradable. The examples that had a viscosity greater than or equal to 550 Pa*s for both emollients were Examples E, G, and H. Examples E-1 and 2 are not preferred because both examples had a noticeable foul odor that could be offensive to many consumers.

Examples G-1 and 2 and H-1 and 2 have a viscosity greater than or equal to 550 Pa*s and have no noticeable off-putting smell. In addition, both examples were stable emulsions. The emulsifier in Examples H-1 and 2 was cetearyl olivate and sorbitan olivate. It is believed that other emulsifiers that include a mixture of waxy esters made from fatty alcohols and fatty acids derived from natural sources (e.g., olive, palm, corn, palm, rapeseed, soybean, sunflower, coconut, tallow, canola, castor) with a carbon chain length ranging from C12-C22 could be used in stable skin care compositions that have sufficient viscosity (e.g., ≥550 Pa*s).

In some examples, G-1 and 2 may be consumer preferred because these examples had the highest viscosity (e.g., ≥900 Pa*s). The emulsifier in G-1 and 2 was Polyglyceryl-3 Cetearyl Ether Olivate.

TABLE 4

| | Ex. 1 (wt. %) | Ex. 2 (wt. %) | Ex. 3 (wt. %) | Ex. 4 (wt. %) | Ex. 5 (wt. %) | Ex. 6 (wt. %) |
|---|---|---|---|---|---|---|
| Isohexadecene | 0 | 0 | 6 | 6 | 6 | 6 |
| Shea Butter Ethyl Esters | 3 | 3 | 3 | 3 | 0 | 0 |
| Isoamyl Laurate[1] | 0 | 0 | 0 | 0 | 3 | 3 |
| Triheptanoin | 1.3 | 1.3 | 0 | 0 | 1.5 | 0 |
| Stearyl Alcohol | 1 | 1 | 1 | 0 | 1 | 1 |
| Cetyl Alcohol | 0.8 | 0.8 | 0.8 | 0 | 0.8 | 0.8 |
| Behenyl Alcohol | 0.6 | 0.6 | 0.6 | 0 | 0.6 | 0.6 |
| Polyglyceryl-3 Methylglucose Distearate | 0 | 0 | 0 | 2.6 | 0 | 0 |
| Polyglyceryl-3 Cetearyl Ether Olivate[4] | 0.4 | 0.2 | 0.4 | 0.4 | 0.4 | 0.6 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Hydroxyacetophenone | 0.15 | 0.15 | 0.15 | 0.15 | 0.15 | 0.15 |
| Distarch Phosphate | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0 | 0.5 | 0 | 0 | 0 | 0 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 1.5 | 1.5 | 1.5 | 1.5 | 0 | 1.5 |
| Sodium Acrylate/Sodium Acryloyldimethyl Taurate Copolymer & C15-19 Alkane* & Polyglyceryl-6 Laurate* & Polyglycerin-6[10] | 1.6 | 1.6 | 1.6 | 1.6 | 1.6 | 1.6 |
| Water | Q.S. to Volume | | | | | |

TABLE 5

| | Ex. 7 (wt. %) | Ex. 8 (wt. %) | Ex. 9 (wt. %) | Ex. 10 (wt. %) | Ex. 11 (wt. %) | Ex. 12 (wt. %) |
|---|---|---|---|---|---|---|
| Isohexadecene | 6 | 3 | 1.3 | 6 | 6 | 6 |
| Isoamyl Laurate[1] | 3 | 3 | 3 | 3 | 3 | 3 |
| Stearyl Alcohol | 1 | 1 | 1 | 1 | 1 | 0 |
| Cetyl Alcohol | 0.8 | 0.8 | 0.8 | 0.8 | 0.8 | 0 |
| Behenyl Alcohol | 0.6 | 0.6 | 0.6 | 0.6 | 0.6 | 0 |
| Polyglyceryl-3 Cetearyl Ether Olivate[4] | 0.2 | 0.2 | 0.2 | 0.1 | 0.1 | 3 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |

TABLE 5-continued

| | Ex. 7 (wt. %) | Ex. 8 (wt. %) | Ex. 9 (wt. %) | Ex. 10 (wt. %) | Ex. 11 (wt. %) | Ex. 12 (wt. %) |
|---|---|---|---|---|---|---|
| Disodium EDTA | 0.05 | 0.05 | 0.05 | 0.05 | 0.05 | 0.05 |
| Acrylates/C10-30 Alkyl Acrylate Crosspolymer[5] | 0 | 0 | 0 | 0.05 | 0 | 0 |
| Hydroxyacetophenone | 0.15 | 0.15 | 0.15 | 0.15 | 0.15 | 0.15 |
| Distarch Phosphate | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0.5 | 0.5 | 0.5 | 0.5 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 1.5 | 1.5 | 1.5 | 1.5 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.6 | 1.6 | 1.6 | 1.6 | 1.6 | 1.6 |
| Water | | | Q.S. to Volume | | | |

TABLE 6

| | Ex. 13 (wt. %) | Ex. 14 (wt. %) | Ex. 15 (wt. %) | Ex. 16 (wt. %) | Ex. 17 (wt. %) | Ex. 18 (wt. %) |
|---|---|---|---|---|---|---|
| Isohexadecene | 6 | 6 | 6 | 6 | 6 | 6 |
| Shea Butter Ethyl Esters | 0 | 0 | 0 | 0 | 0 | 0 |
| Isoamyl Laurate[1] | 3 | 3 | 3 | 3 | 3 | 3 |
| Stearyl Alcohol | 0 | 0 | 1 | 1 | 1 | 1 |
| Cetyl Alcohol | 0 | 0 | 0.8 | 0.8 | 0.8 | 0.8 |
| Behenyl Alcohol | 0 | 0 | 0.6 | 0.6 | 0.6 | 0.6 |
| Polyglyceryl-3 Cetearyl Ether Olivate[4] | 2 | 0.2 | 0.2 | 0.2 | 0.2 | 0.2 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Acrylates/C10-30 Alkyl Acrylate Crosspolymer[5] | 0 | 0.1 | 0 | 0 | 0 | 0 |
| Hydroxyacetophenone | 0.15 | 0.15 | 0.15 | 0.15 | 0.15 | 0.15 |
| Distarch Phosphate | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0.5 | 0.5 | 0.5 | 0.5 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 1.5 | 1.5 | 1.5 | 1.5 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.6 | 1.6 | 0.75 | 1.25 | 1.8 | 2 |
| Water | | | Q.S. to Volume | | | |

TABLE 7

| | Ex. 19 (wt. %) | Ex. 20 (wt. %) | Ex. 21 (wt. %) | Ex. 22 (wt. %) | Ex. 23 (wt. %) | Ex. 24 (wt. %) |
|---|---|---|---|---|---|---|
| Isohexadecene | 0 | 1.3 | 1.3 | 1.3 | 3 | 3 |
| Isoamyl Laurate[1] | 4.3 | 3 | 3 | 3 | 3 | 3 |
| Stearyl Alcohol | 0 | 1 | 1 | 1 | 0.8 | 1 |
| Cetyl Alcohol | 0 | 0.8 | 0.8 | 0.8 | 0.65 | 0.8 |
| Behenyl Alcohol | 0 | 0.6 | 0.6 | 0.6 | 0.5 | 0.6 |
| Polyglyceryl-3 Cetearyl Ether Olivate[4] | 0.4 | 0.2 | 0.2 | 0.2 | 0.2 | 0.2 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |

TABLE 7-continued

| | Ex. 19 (wt. %) | Ex. 20 (wt. %) | Ex. 21 (wt. %) | Ex. 22 (wt. %) | Ex. 23 (wt. %) | Ex. 24 (wt. %) |
|---|---|---|---|---|---|---|
| Acrylates/C10-30 Alkyl Acrylate Crosspolymer[5] | 0.1 | 0 | 0 | 0 | 0 | 0 |
| Hydroxyacetophenone | 0.15 | 0.15 | 0.15 | 0.15 | 0.15 | 0.15 |
| Distarch Phosphate | 0 | 5 | 5 | 0 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0 | 0.5 | 0 | 0.5 | 0.5 | 0.5 |
| Titanium Dioxide | 0 | 0.15 | 0 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 0 | 0 | 1.5 | 1.5 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.8 | 1.6 | 1.6 | 1.6 | 1.6 | 1.25 |
| Water | | | Q.S. to Volume | | | |

TABLE 8

| | Ex. 25 (wt. %) | Ex. 26 (wt. %) | Ex. 27 (wt. %) | Ex. 28 (wt. %) | Ex. 29 (wt. %) | Ex. 30 (wt. %) |
|---|---|---|---|---|---|---|
| Isohexadecene | 0 | 0 | 0 | 0 | 0 | 1.3 |
| Isoamyl Laurate[1] | 3 | 3 | 3 | 3 | 3 | 3 |
| Triheptanoin | 1.3 | 1.3 | 3 | 1.3 | 1.3 | 0 |
| Stearyl Alcohol | 1 | 0.8 | 1 | 1 | 1 | 1 |
| Cetyl Alcohol | 0.8 | 0.65 | 0.8 | 0.8 | 0.8 | 0.8 |
| Behenyl Alcohol | 0.6 | 0.5 | 0.6 | 0.6 | 0.6 | 0.6 |
| Polyglyceryl-3 Cetearyl Ether Olivate[4] | 0.3 | 0.4 | 0.4 | 0.2 | 0.2 | 0.2 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Hydroxyacetophenone | 0.15 | 0.15 | 0.15 | 0.15 | 0.15 | 0.15 |
| Distarch Phosphate | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0.5 | 0.5 | 0.5 | 0.5 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 1.5 | 1.5 | 1.5 | 1.5 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.6 | 1.6 | 1.6 | 1.8 | 2 | 1.8 |
| Water | | | Q.S. to Volume | | | |

TABLE 9

| | Ex. 31 (wt. %) | Ex. 32 (wt. %) | Ex. 33 (wt. %) | Ex. 34 (wt. %) | Ex. 35 (wt. %) | Ex. 36 (wt. %) |
|---|---|---|---|---|---|---|
| Isohexadecene | 1.3 | 0 | 0 | 0 | 0 | 0 |
| Isoamyl Laurate[1] | 3 | 1.3 | 1.3 | 3 | 3 | 3 |
| Isoamyl Laurate[2] | 0 | 0 | 0 | 0 | 0 | 0 |
| Triheptanoin | 0 | 3 | 3 | 6 | 6 | 6 |
| Stearyl Alcohol | 1 | 1 | 1 | 1 | 1 | 1 |
| Cetyl Alcohol | 0.8 | 0.8 | 0.8 | 0.8 | 0.8 | 0.8 |
| Behenyl Alcohol | 0.6 | 0.6 | 0.6 | 0.6 | 0.6 | 0.6 |
| Polyglyceryl-3 Cetearyl Ether Olivate[4] | 0.2 | 0.4 | 0.4 | 0.4 | 0.4 | 0.2 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Hydroxyacetophenone | 0.15 | 0.15 | 0.15 | 0.15 | 0.15 | 0.15 |

TABLE 9-continued

| | Ex. 31 (wt. %) | Ex. 32 (wt. %) | Ex. 33 (wt. %) | Ex. 34 (wt. %) | Ex. 35 (wt. %) | Ex. 36 (wt. %) |
|---|---|---|---|---|---|---|
| Distarch Phosphate | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0.5 | 0.5 | 0.5 | 0.5 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 1.5 | 1.5 | 1.5 | 0 | 0 | 0 |
| Sodium Acrylate/Sodium Acryloyldimethyl Taurate Copolymer & C15-19 Alkane* & Polyglyceryl-6 Laurate* & Polyglycerin-6[10] | 2 | 1.6 | 1.8 | 1.8 | 1.6 | 1.8 |
| Water | | | Q.S. to Volume | | | |

TABLE 10

| | Ex. 37 (wt. %) | Ex. 38 (wt. %) | Ex. 39 (wt. %) | Ex. 40 (wt. %) | Ex. 41 (wt. %) | Ex. 42 (wt. %) |
|---|---|---|---|---|---|---|
| Isohexadecene | 0 | 0 | 6 | 0 | 0 | 1.3 |
| Shea Butter Ethyl Esters | 0 | 0 | 3 | 0 | 0 | 0 |
| Isoamyl Laurate[1] | 3 | 3 | 0 | 3 | 0 | 0 |
| Isoamyl Laurate[2] | 0 | 0 | 0 | 0 | 3 | 3 |
| Triheptanoin | 1.3 | 1.3 | 0 | 6 | 1.3 | 0 |
| Stearyl Alcohol | 0.1 | 0.1 | 1 | 1 | 1 | 1 |
| Cetyl Alcohol | 0.08 | 0.08 | 0.8 | 0.8 | 0.8 | 0.8 |
| Behenyl Alcohol | 0.06 | 0.06 | 0.6 | 0.6 | 0.6 | 0.6 |
| Polyglyceryl-3 Cetearyl Ether Olivate[4] | 0.1 | 0.1 | 0.4 | 0.4 | 0.4 | 0.2 |
| Panthenol | 0.5 | 0.5 | 1 | 1 | 1 | 1 |
| Glycerin | 7 | 7 | 15 | 20 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Hydroxyacetophenone | 0.15 | 0.15 | 0.15 | 0.15 | 0.15 | 0.15 |
| Distarch Phosphate | 0 | 0 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0 | 0.5 | 0.5 | 0.5 |
| Titanium Dioxide | 0 | 0 | 0.15 | 0.15 | 0.15 | 0.15 |
| Palmitoyl Pentapeptide-4[8] | 0.353 | 0.353 | 0.353 | 0.353 | 0.353 | 0.353 |
| Fragrance | 0 | 0 | 0 | 0 | 0 | 0.013 |
| Dimethicone, Dimethiconol[9] | 0 | 0 | 0 | 0 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1 | 1.4 | 1.6 | 1.8 | 1.8 | 1.8 |
| Water | | | Q.S. to Volume | | | |

TABLE 11

| | Ex. 43 (wt. %) | Ex. 44 (wt. %) | Ex. 45 (wt. %) | Ex. 46 (wt. %) | Ex. 47 (wt. %) | Ex. 48 (wt. %) |
|---|---|---|---|---|---|---|
| Isoamyl Laurate[1] | 3 | 0 | 0 | 0 | 0 | 0 |
| Isoamyl Laurate[2] | 0 | 0 | 0 | 3 | 3 | 3 |
| Triheptanoin | 0 | 1.3 | 1.3 | 0 | 0 | 0 |
| Caprylic/Capric Triglyceride[3] | 6 | 0 | 0 | 1.3 | 1.3 | 1.3 |
| Stearyl Alcohol | 1 | 1 | 1 | 0.9 | 0.9 | 0.9 |
| Cetyl Alcohol | 0.8 | 0.8 | 0.8 | 0.8 | 0.8 | 0.8 |
| Behenyl Alcohol | 0.6 | 0.6 | 0.6 | 0.7 | 0.7 | 0.7 |
| Polyglyceryl-3 Cetearyl Ether Olivate[4] | 0.4 | 0.4 | 0.4 | 0.4 | 0.4 | 0.4 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Hydroxyacetophenone | 0.15 | 0.15 | 0.15 | 0.15 | 0.15 | 0.15 |

TABLE 11-continued

| | Ex. 43 (wt. %) | Ex. 44 (wt. %) | Ex. 45 (wt. %) | Ex. 46 (wt. %) | Ex. 47 (wt. %) | Ex. 48 (wt. %) |
|---|---|---|---|---|---|---|
| Distarch Phosphate | 5 | 5 | 5 | 0 | 0 | 0 |
| *Zea Mays* Corn Starch[6] | 0 | 0 | 0 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0.5 | 0.5 | 0.5 | 0.5 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 0 | 1.5 | 1.5 | 1.5 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.8 | 1.8 | 1.4 | 1.7 | 1.7 | 1.7 |
| Water | | | Q.S. to Volume | | | |

TABLE 12

| | Ex. 49 (wt. %) | Ex. 50 (wt. %) | Ex. 51 (wt. %) | Ex. 52 (wt. %) | Ex. 53 (wt. %) | Ex. 54 (wt. %) |
|---|---|---|---|---|---|---|
| Isohexadecene | 0 | 0 | 1.3 | 0 | 0 | 0 |
| Isoamyl Laurate[2] | 3 | 3 | 3 | 3 | 3 | 3 |
| Caprylic/Capric Triglyceride[3] | 1.3 | 0 | 0 | 0 | 0 | 0 |
| Stearyl Alcohol | 0.9 | 0.9 | 0.9 | 0.9 | 0.9 | 0.9 |
| Cetyl Alcohol | 0.8 | 0.8 | 0.8 | 0.8 | 0.8 | 0.8 |
| Behenyl Alcohol | 0.7 | 0.7 | 0.7 | 0.7 | 0.7 | 0.7 |
| Polyglyceryl-3 Cetearyl Ether Olivate[4] | 0.4 | 0.2 | 0.2 | 0.2 | 0.2 | 0.2 |
| Panthenol | 1 | 1 | 1 | 1 | 1 | 1 |
| Glycerin | 15 | 15 | 15 | 15 | 15 | 15 |
| Niacinamide | 5 | 5 | 5 | 5 | 5 | 5 |
| Disodium EDTA | 0.05 | 0.05 | 0.05 | 0.05 | 0.05 | 0.05 |
| Hydroxyacetophenone | 0.15 | 0.15 | 0.15 | 0.15 | 0.15 | 0.15 |
| *Zea Mays* Corn Starch[6] | 5 | 5 | 5 | 5 | 5 | 5 |
| Phenoxyethanol | 0.375 | 0.375 | 0.375 | 0.375 | 0.375 | 0.375 |
| Ethylhexylglycerin | 0.2 | 0.2 | 0.2 | 0.2 | 0.2 | 0.2 |
| Pearlescent Agents[7] | 0.5 | 0.5 | 0.5 | 0.5 | 0.5 | 0.5 |
| Titanium Dioxide | 0.15 | 0.15 | 0.15 | 0.15 | 0.15 | 0.15 |
| Palmitoyl Pentapeptide-4[8] | 0.353 | 0.353 | 0.353 | 0.353 | 0.353 | 0.353 |
| Dimethicone, Dimethiconol[9] | 1.5 | 1.5 | 1.5 | 1.5 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.7 | 1.8 | 1.8 | 1.8 | 1.8 | 1.8 |
| Water | | | Q.S. to Volume | | | |

TABLE 13

| | Ex. 55 (wt. %) | Ex. 56 (wt. %) | Ex. 57 (wt. %) | Ex. 58 (wt. %) |
|---|---|---|---|---|
| Isohexadecene | 6 | 0 | 0 | 1.3 |
| Isoamyl Laurate[1] | 3 | 3 | 0 | 0 |
| Isoamyl Laurate[2] | 0 | 0 | 3 | 3 |
| Triheptanoin | 0 | 6 | 1.3 | 0 |
| Stearyl Alcohol | 1 | 1 | 1 | 1 |
| Cetyl Alcohol | 0.8 | 0.8 | 0.8 | 0.8 |
| Behenyl Alcohol | 0.6 | 0.6 | 0.6 | 0.6 |
| Polyglyceryl-3 Cetearyl Ether Olivate[4] | 0.2 | 0.2 | 0.4 | 0.2 |
| Panthenol | 1 | 1 | 1 | 1 |
| Glycerin | 15 | 15 | 15 | 15 |
| Niacinamide | 5 | 5 | 5 | 5 |
| Disodium EDTA | 0.05 | 0.05 | 0.05 | 0.05 |
| Hydroxyacetophenone | 0.15 | 0.15 | 0.15 | 0.15 |
| Distarch Phosphate | 0 | 0 | 5 | 5 |
| *Zea Mays* Corn Starch[6] | 5 | 5 | 0 | 0 |
| Phenoxyethanol | 0.375 | 0.375 | 0.375 | 0.375 |
| Ethylhexylglycerin | 0.2 | 0.2 | 0.2 | 0.2 |

TABLE 13-continued

| | Ex. 55 (wt. %) | Ex. 56 (wt. %) | Ex. 57 (wt. %) | Ex. 58 (wt. %) |
|---|---|---|---|---|
| Pearlescent Agents[7] | 0 | 0 | 0.5 | 0.5 |
| Titanium Dioxide | 0 | 0 | 0.15 | 0.15 |
| Palmitoyl Pentapeptide-4[8] | 0 | 0 | 0.353 | 0.353 |
| Fragrance | 0 | 0 | 0.013 | 0.013 |
| Dimethicone, Dimethiconol[9] | 0 | 0 | 1.5 | 1.5 |
| Sodium Acrylate/Sodium Acryloyldimethyl Taurate Copolymer & C15-19 Alkane* & Polyglyceryl-6 Laurate* & Polyglycerin-6[10] | 1.6 | 1.6 | 1.8 | 1.8 |
| Water | | Q.S. to Volume | | |

Tradenames and Suppliers for Table 4 to Table 13:

1. Mackaderm® LIA MB from Solvay
2. Dermafeel® sensolv MB
3. Mryitol® 318 from BASF®
4. Galolive® Bioten from Acme-Hardesty®
5. Pemulen™ EZ-4U from Lubrizol®

6. AMAZE® HTP Pure from Nouryon®
7. Examples of pearlescent agents include titanium dioxide (and) synthetic fluorphlogopite and titanium dioxide and mica
8. Promatrixyl® from Sederma®
9. DC1503 from Dow®
10. SEPILIFE™ NUDE from Seppic® Corporation plant-based & renewable Combinations A. A skin care composition comprising:
   a. a continuous phase comprising:
      i. a polymer comprising an acrylate/taurate copolymer;
      ii. water;
   b. a dispersed phase comprising:
      i. two or more emollients comprising:
         1. a liquid emollient; wherein the liquid emollient comprises alkanes, esters, triglycerides, or combinations thereof;
         2. a fatty alcohol having an average carbon chain length ranging from about 12 to about 22, preferably from about 12 to about 18; or a liquid emollient; wherein the liquid emollient comprises alkanes, esters, triglycerides, or combinations thereof;
   c. an emulsifier comprising polyglyceryl-3 cetearyl ether olivate.

B. The skin composition according to Paragraph A, wherein the acrylate/taurate copolymer is a sodium acrylate/sodium acryloyldimethyl taurate copolymer.

C. The skin care composition according to Paragraphs A-B, wherein the composition further comprises at least one of the following C15-19 Alkane & Polyglyceryl-6 Laurate, Polyglycerin-6, lauryl glucoside, or a combination thereof.

D. The skin care composition according to Paragraphs A-C, wherein the emollients and emulsifiers are naturally derived.

E. The skin care composition according to Paragraphs A-D, wherein the composition is formulated without polyacrylamides.

F. The skin care composition according to Paragraphs A-E, wherein the composition is formulated without phenoxyethanol.

G. The skin care composition according to Paragraphs A-F, wherein the two or more emollients and the one or more emulsifiers are formulated without petroleum derived ingredients.

H. The skin care composition according to Paragraphs A-G, wherein the composition is clean.

I. The skin care composition according to Paragraphs A-H, wherein the composition is formulated without ethoxylated ingredients.

J. The skin care composition according to Paragraphs A-I, wherein the composition is formulated without emulsifiers containing polyethylene glycol repeat units.

K. The skin care composition according to Paragraphs A-K, wherein the composition further comprises methylheptylglycerin.

L. The skin care composition according to Paragraphs A-K, wherein the composition comprises from about 0.3% to about 1.5% of the acrylate/taurate copolymer.

M. The skin care composition according to Paragraphs A-L, wherein the composition comprises from about 0.2% to about 8% fatty alcohol, preferably from about 0.5% to about 5% fatty alcohol, more preferably from about 1% to about 4% fatty alcohol, and most preferably from about 1.5% to about 3.5% fatty alcohol.

N. The skin care composition according to Paragraphs A-M, wherein the composition comprises from about 0.10% to about 2% emulsifier, preferably from about 0.2% to about 1.5% emulsifier, more preferably from about 0.4% to about 1.2% emulsifier, and most preferably from about 0.6% to about 0.8% emulsifier.

O. The skin care composition according to Paragraphs A-N, wherein the emollient comprises isohexadecene and/or triheptanoin.

P. The skin care composition according to Paragraphs A-O, wherein the skin care composition is a moisturizer.

Q. The skin care composition according to Paragraph P, wherein the moisturizer comprises from about 0.2% to about 3% acrylate/taurate copolymer, preferably from about 0.5% to about 2.5% acrylate/taurate copolymer, more preferably from about 0.75% to about 2.2% acrylate/taurate copolymer, and even more preferably from about 1.5% to about 1.9% acrylate/taurate copolymer.

R. The skin care composition according to Paragraphs P-Q, wherein the moisturizer comprises a viscosity at about 0.10 $s^{-1}$ is greater than or equal to 550 Pa*s, preferably greater than or equal to 1500 Pa*s, more preferably greater than or equal to 2000 Pa*s according to the Rheology Test Method.

S. The skin care composition according to Paragraphs A-O, wherein the skin care composition is a serum.

T. The skin care composition according to Paragraph S, wherein the serum composition comprises 0.1% to about 1.5% acrylate/taurate copolymer, preferably from about 0.2% to about 1.25% acrylate/taurate copolymer, more preferably from about 0.4% to about 1% acrylate/taurate copolymer, and even more preferably from about 0.5% to about 0.75% acrylate/taurate copolymer.

U. The skin care composition according to Paragraphs S-T, wherein the serum comprises a viscosity at 0.10 $s^{-1}$ of about 20 to about 500 Pa*s, preferably from about 30 to about 300 Pa*s, and more preferably from about 50 to about 20 Pa*s.

V. The skin care composition according to Paragraphs A-U, wherein the composition comprises ≤25 ingredients that need to be reported on the INCI, preferably ≤20 ingredients, more preferably ≤15 ingredients, and even more preferably ≤12 ingredients.

W. Use of a combination of an acrylate/taurate copolymer and an emulsifier comprising polyglyceryl-3 cetearyl ether olivate in a skin care composition as defined in Paragraphs A-V for providing a stable and/or clean composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition comprising:

a. a continuous phase comprising:

i. a polymer comprising an acrylate/taurate copolymer;

ii. water;

b. a dispersed phase comprising:

i. two or more emollients comprising:

1. A liquid emollient; wherein the liquid emollient comprises alkanes, esters, triglycerides, or combinations thereof;

2. A fatty alcohol having an average carbon chain length ranging from about 12 to about 22;

c. an emulsifier consisting of polyglyceryl-3 cetearyl ether olivate;

wherein the composition comprises a viscosity of greater than or equal to 900 Pa*s at a shear rate of 0.10 $s^{-1}$ and at 25° C. according to the Rheology Test Method; and wherein the composition is physically stable.

2. The skin care composition of claim 1, wherein the acrylate/taurate copolymer comprises a sodium acrylate/sodium acryloyldimethyl taurate copolymer.

3. The skin care composition of claim 2, wherein the polymer further comprises at least one of the following C15-19 alkane & polyglyceryl-6 laurate, polyglycerin-6, lauryl glucoside, or a combination thereof.

4. The skin care composition of claim 1, wherein the emollients and emulsifiers are naturally derived.

5. The skin care composition of claim 1, wherein the composition is formulated without polyacrylamides.

6. The skin care composition of claim 1, wherein the composition is formulated without phenoxyethanol.

7. The skin care composition of claim 1, wherein the composition is clean.

8. The composition of claim 1, wherein the average carbon chain length of the fatty alcohol is from about 12 to about 18.

9. The composition of claim 1, wherein the composition is formulated without ethoxylated ingredients.

10. The composition of claim 1, wherein the composition is formulated without emulsifiers containing polyethylene glycol repeat units.

11. The composition of claim 1, wherein the composition further comprises methylheptylglycerin.

12. The composition of claim 1 wherein the composition comprises from about 0.3% to about 1.5% of the acrylate/taurate copolymer.

13. The composition of claim 1, wherein the composition comprises from about 0.25% to about 2.5% of the fatty alcohol.

14. The composition of claim 1, wherein the composition comprises from about 0.2% to about 1.0% of the emulsifier.

15. The composition of claim 1, wherein the composition is formulated without silicones.

16. The composition of claim 15, wherein the composition is formulated without petroleum-based emollients.

17. The composition of claim 1, wherein the composition is free of sulfates, parabens, formaldehyde, phthalates, and mineral oils.

18. The composition of claim 1, wherein the composition comprises from about 0.2% to about 1.5% of the emulsifier.

* * * * *